United States Patent [19]
Charlton et al.

[11] 3,933,996
[45] Jan. 20, 1976

[54] COMPOSITION COMPRISING RADIOACTIVE LABELED-FIBRINOGEN AND ALBUMIN

[75] Inventors: John Cecil Charlton; David Lawrence Gravett, both of Amersham, England

[73] Assignee: The Radiochemical Centre Limited, Amersham, England

[22] Filed: June 19, 1973

[21] Appl. No.: 371,529

[30] Foreign Application Priority Data
June 22, 1972 United Kingdom............... 29401/72

[52] U.S. Cl. ..................... 424/1; 424/95; 424/177
[51] Int. Cl.² ................. A61K 43/00; A61K 35/16; A61K 37/02
[58] Field of Search ............. 62/56; 424/1, 95, 101, 424/177

[56] References Cited
UNITED STATES PATENTS

| | | | |
|---|---|---|---|
| 2,085,391 | 6/1937 | Reichel | 424/101 X |
| 3,674,900 | 7/1972 | Thompson | 424/1 |
| 3,784,453 | 1/1974 | Dworkin et al. | 424/1 |
| 3,803,299 | 4/1974 | Novel | 424/1 |

OTHER PUBLICATIONS

Harrow, B., Textbook of Biochemistry, 5th Ed., Philadelphia, W. B. Saunders Co., 1950, p. 406.

*Primary Examiner*—Benjamin R. Padgett
*Assistant Examiner*—Christine M. Nucker
*Attorney, Agent, or Firm*—Wenderoth, Lind & Ponack

[57] ABSTRACT

The stability of fibrinogen is improved by mixing it with albumin, preferably at least 5 parts by weight of albumin per part by weight of fibrinogen. By this invention, iodinated ($^{125}I$) human fibrinogen can be stabilised with human serum albumin for use in the diagnosis of thrombi.

10 Claims, No Drawings

COMPOSITION COMPRISING RADIOACTIVE LABELED-FIBRINOGEN AND ALBUMIN

This invention relates to protein materials, and particularly to fibrinogen. Fibrinogen is an inherently unstable material, much more unstable than the other common blood proteins. This is because the molecule has been cunningly fashioned to undergo polymerisation when triggered by the appropriate enzyme (thrombin). This removes protective groups from the ends of the fibrinogen molecule, which can then polymerise to give fibrin-containing clots. This is the basic mechanism of blood coagulation at a cut or damaged surface. However, fibrinogen is inherently unstable even when precautions have been taken to remove enzymes such as thrombin. Thus, the Extra Pharmacopoeia says: "It is a white powder or friable solid, readily soluble in water to form a colourless solution which may clot spontaneously on standing." On account of this well recognised instability in aqueous solution, fibrinogen is supplied as the freeze-dried solid and is dissolved in water immediately before use. The British Pharmacopoeia, for example, states: "It may be prepared from liquid human plasma by precipitating with organic solvents under controlled conditions of pH, ionic concentration, and temperature, dissolving the precipitate in a solution of sodium chloride and sodium citrate, and drying from the frozen state."

It is a matter of considerable difficulty to obtain fibrinogen for therapeutic purposes (as, for example, described in the British Pharmacopoeia) which is pure and stable, but the problems have been solved, and such a product is a normal article of commerce.

In recent years, iodinated ($^{125}$I) human fibrinogen has come into extensive use in the diagnosis of thrombi in the deep veins of the leg. Fibrinogen, as a human blood product which cannot be heat-treated to destroy viruses, carries a risk of transmission of serum hepatitis. When used therapeutically, fibrinogen is employed essentially as a lifesaving measure, and the small risk of serum hepatitis does not preclude its use. When used as a diagnostic agent, where it is not life-saving in the usual meaning of the term, the risk of serum hepatitis must be reduced to the lowest practicable level. In practice this means that fibrinogen for diagnostic work is prepared from the plasma of a small number of donors who are regularly submitted to a comprehensive clinical testing programme to ensure as far as is possible that they will not transmit serum hepatitis. This plasma is processed specially, and on a small chemical scale, and, for reasons which are not apparent, often lacks the stability associated with the normal article of commerce.

the iodinated ($^{125}$I) human fibrinogen is also supplied as the freeze dried solid, and lack of stability has been a major problem. This lack of stability is manifested primarily by the conversion of the water-soluble fibrinogen into a water-insoluble form, presumably fibrin polymer. While it is possible that the processes of iodination, purification and freeze-drying introduce an additional element of instability, there is nevertheless a close correlation between the stability of the final product and the nature of the fibrinogen used for iodination. A single batch of fibrinogen is employed for a number of preparations of the iodinated product. These individual preparations from a single batch of starting material all show similar stability: some batches of starting material give consistently stable iodinated fibrinogen, whereas other batches give consistently unstable iodinated fibrinogen. While we do not wish to be bound by any theory, it appears to us that a possible explanation is that the fibrinogen molecules may have undergone damage at some stage in the process, e.g. in the collection or storage of the blood plasma, or in the separation of the fibrinogen from the plasma, and that this leads to an inherently unstable product, in that while the chemical processes involved do not distinguish between the damaged and undamaged molecules (in this connection it must be remembered that fibrinogen is an exceptionally large molecule, MW 340,000), damage to the ends of the molecules makes them more subject to polymerisation, with the resultant formation of fibrin polymer.

It is an object of the invention to provide a means of reducing or preventing the unwanted decomposition of fibrinogen.

The present invention provides a solid product comprising fibrinogen or a derivative thereof together with albumin in an amount sufficient to reduce or prevent unwanted decomposition of the fibrinogen.

The invention also provides a method of making the solid product defined above, which method comprises removing water from an aqueous solution or suspension of the fibrinogen and the albumin. This removal of water may conveniently be effected by freeze-drying; alternatively it is possible in principle to precipitate the protein mixture from aqueous solution or suspension by the use of organic liquids.

As the fibrinogen, there may be used the protein itself or a derivative thereof, for example an iodinated derivative, particularly iodinated ($^{125}$I) or ($^{131}$I) fibrinogen. Where the product is to be used in the treatment of human beings, the fibrinogen will normally be human fibrinogen. The nature of the fibrinogen or derivative is not critical to the present invention.

Where the product is to be used in the treatment of human beings, the albumin will normally be human serum albumin, but for other purposes animal albumin may be employed. It should be noted that the albumin does not necessarily have to be pure. Thus, in place of pure human serum albumin, it may be possible, though not preferred, to use human plasma or partially purified fractions of human serum proteins containing, and preferably rich in, human serum albumin.

It is known to add albumin to iodinated and other labelled protein supplied in solution, either to minimise absorption of the labelled protein on glassware or to minimise radiolytic decomposition by diluting the labelled protein.

The present invention is concerned with neither of these effects. It is aimed primarily at the reduction or prevention of unwanted transformation of fibrinogen into an insoluble form, not the reduction or prevention of adsorption of the protein to glassware. Furthermore, the effect against which protection is sought is not one concerned with the effect of radiation or of radiolytic products on the fibrinogen molecule. The evidence on this latter point is that we can make batches of labelled fibrinogen, at the same specific activities, but with enormously varying degrees of stability. If one were dealing with a radiation effect the degrees of stability would be very similar. The protective effect upon fibrinogen achieved by the use of serum albumin according to the present invention is great, and, as shown in the examples, can render fit for use a preparation which, without it, could be useless in practical circumstances. The magnitude of the protective effect was surprising to the inventors.

We have obtained good results by using about 20 parts of serum albumin per part by weight of fibrinogen, and we expect that protection at least as good can be obtained by the use of larger proportions of albumin, e.g. up to 1,000 parts by weight of albumin per part by weight of fibrinogen. The use of larger proportions of albumin per part by weight of fibrinogen might be particularly appropriate if it were thought desirable to maintain a minimum weight of albumin in a container even though the weight of fibrinogen employed was much smaller than the weight of 1 mg given in the Examples that follow (as would be the case, for example, if to economise in the use of fibrinogen, a specific activity much greater than 200 µCi/mg fibrinogen were employed).

Our experiments indicate that the use of 10 parts by weight of albumin per part by weight of fibrinogen gives excellent results, while the use of 5 parts by weight of albumin gives rise to products having an inferior stability which is nevertheless very much better than that obtainable without albumin. We infer that at least 1 part by weight of albumin per part by weight of fibrinogen is probably required to confer a significant improvement in stability over unprotected fibrinogen.

As the protective effect obtained by the use of albumin according to this invention is believed not to be a radiolytic effect, it follows that the specific activity of the labelled fibrinogen is not critical. For example, iodinated ($^{125}$I) human fibrinogen can be prepared with a specific activity up to 200 µCi/mg fibrinogen and greater, and fibrinogen with no specific activity or with any activity in this range can be protected by this invention.

The amount of fibrinogen in each batch of solid product being protected is not critical. Iodinated ($^{125}$I) human fibrinogen is frequently sold in 1 mg portions. The invention is particularly applicable to the protection of such portions ranging in size up to 10 mg fibrinogen, but is also suitable for the protection of larger amounts of fibrinogen.

The solid product of this invention may be prepared by freeze-drying a solution or suspension, e.g. an aqueous solution or suspension of the fibrinogen and the albumin. The solids content of this solution or suspension is not critical. The albumin and the fibrinogen may be added to the liquid, e.g. water, together or in either order. The solution or suspension may be freeze-dried in a manner which is normal for freeze-drying fibrinogen.

The following experimental data illustrate the invention.

After iodination the iodinated ($^{125}$I) human fibrinogen has specific activity of 100 to 200 µCi/mg fibrinogen and is dissolved at a concentration of about 1 mg/ml in an aqueous solution containing sodium citrate (0.75%) and sodium chloride (0.65%). 1.1 ml portions of this solution are dispensed into vials and freeze-dried. In experiments in which the effect of albumin is studied, human albumin is added to give a concentration of about 20 mg/ml prior to freeze-drying. The vials are stored at the temperatures stated, and the times stated, and then water is added (1.1 ml) and swirled gently at room temperature for 10 minutes. The soluble radioactive material is removed and the recovery of radioactivity determined. This recovery of soluble radioactive material, expressed as a percentage, is designated "R". It consists of iodinated ($^{125}$I) human fibrinogen plus various ($^{125}$I) labelled impurities such as iodinated proteins other than fibrinogen, iodinated fibrinogen so denatured as not to be clottable with thrombin, and iodide ion ($^{125}$I). To the soluble material is added bovine thrombin in the presence of human plasma, the clot is separated, and the amount of radioactivity in it is determined. The percentage of clottable fibrinogen in the soluble fraction is designated by C. It will be noted that, since the formation of insoluble material on storage is due to polymerisation of the iodinated ($^{125}$I) human fibrinogen, the amount of soluble fibrinogen decreases while the amount of unclottable impurities remain constant. This means that as R decreases, C must inevitably decrease. In principle, C could decrease more rapidly than required by the above theory, due to other denaturation processes leading to soluble, but non-clottable fibrinogen. The diagnostic use of the material is dependent primarily upon the quantity of soluble, clottable, iodinated ($^{125}$I) human fibrinogen in the vial, that is, upon the mathematical product RC.

EXAMPLE 1

Results on a typical production batch of iodinated ($^{125}$I) human fibrinogen, with and without added human albumin, and stored at 31°C are as follows: Where a range is given, the measurements refer to at least 3 ampoules.

| Days | No Albumin | | Albumin at 20 mg/ml | |
|---|---|---|---|---|
|  | R | C | R | C |
| 0 | 92–94 | 84–91 |  |  |
| 3 | 33–34 | 76–80 |  |  |
| 5 | 9–13 | 57–63 | 95–97 | 90–91 |
| 9 |  |  | 72–95 | 88–91 |
| 14 |  |  | 87 | 86 |

EXAMPLE 2

Results on material prepared from a batch of fibrinogen, known to give a highly unstable product, and stored at + 2°C (the recommended storage temperature) and at + 31°C are as follows:

At 2°C.

| Days | No albumin | | Albumin at 20 mg/ml | |
|---|---|---|---|---|
|  | R | C | R | C |
| 4 | 8–20 | 60–79 | 93–95 | 94 |
| 15 | 0–13 | 20–37 | 96 | 91 |
| 29 | 0–10 | — | 88–91 | 91–92 |

At 31°C.

| Days | No albumin | | Albumin at 20 mg/ml | |
|---|---|---|---|---|
|  | R | C | R | C |
| 4 | 0–18 | 13–60 | 54–59 | 93 |
| 15 | 4–9 | 0–40 | 11–28 | 70–81 |
| 29 | 0–8 | — | 16 | 40 |

EXAMPLE 3

Results on material prepared from another batch of iodinated ($^{125}$I) fibrinogen known to give a highly unstable product, stabilised with 20, 10 and 5 mg of human serum albumin (hsa) per mg of fibrinogen, and stored at −20°C. + 2°C. and + 31°C for up to 63 days, are set out in Table I below. It can readily be seen that the use of as little as 5 mg of albumin per mg of fibrinogen provides a startling improvement in stability.

Unstable batches of fibrinogen have been used for Examples 2 and 3, because the stabilising effect of albumin is more easily demonstrated with such batches in a shorter time. The stabilising effect of albumin is exercised equally on more stable batches of fibrinogen; obviously in commercial operation it would be desirable to start with relatively stable batches of fibrinogen.

The use of albumin according to this invention is capable of providing solid products comprising fibrinogen or a derivative, e.g. an iodinated ($^{125}$I) or ($^{131}$I) derivative, thereof wherein the proportion:

$$\frac{\text{(Soluble clottable fibrinogen present)}}{\text{(Soluble clottable fibrinogen originally provided)}}$$

remains above 0.5 during storage for 1 month at 2°C. Optimally, when the starting batch of fibrinogen is reasonably stable, this proportion will remain above 0.8 during storage for 2 months at 2°C.

4. A solid product as claimed in claim 1, containing at least 5 parts by weight of the albumin per part by weight of the fibrinogen.

5. A solid product as claimed in claim 1, containing 20 – 1,000 parts by weight of the albumin per part by weight of the fibrinogen.

6. A method of making the solid product claimed in claim 1, which comprises removing water from an aqueous solution or suspension of one part by weight of the fibrinogen containing from 1 to 1,000 parts by weight of the albumin to reduce or prevent unwanted decomposition of the fibrinogen.

7. A method as claimed in claim 6, wherein the removal of water is effected by freeze-drying.

8. A method as claimed in claim 6, wherein the aqueous solution or suspension contains 20 – 1,000 parts by weight of the albumin per part by weight of the fibrinogen.

9. A solid product comprising fibrinogen iodinated with iodine-125 and from 5 to 1000 parts by weight of

TABLE 1

|  | Time days | Storage Temp. °C. | R | | | | | | C | | | | | |
|---|---|---|---|---|---|---|---|---|---|---|---|---|---|---|
|  |  |  | −20 | | +2 | | +31 | | −20 | | +2 | | +31 | |
| Stablized | 1 |  | ← | | 93.3 | 97 | → | | ← | | 94.9 | 93.6 | → | |
| 20 mg/ml | 4 |  | 97.8 | 97.3 | 96.6 | 96.7 | 95.2 | 93.1 | 94.3 | 94.2 | 94.7 | 94.2 | 92.9 | 93.9 |
| of hsa | 11 |  | 91.7 | 94.4 | 95.3 | 95.9 | 78.8 | 94.1 | 93.1 | 92.8 | 92.5 | 91.6 | 91.0 | 89.6 |
|  | 26 |  | 96.5 | 96.2 | 96.4 | 96.5 | 70.2 | 40.8 | 91.9 | 91 | 91.2 | | 83.1 | 61.4 |
|  | 53 |  | 96.5 | 97.6 | 93.1 | 96.9 | NIL? | 81.4 | 88 | 86.2 | 76 | 83 | 66.3 | 73.6 |
| 63 |  | 96.4 | 94.2 | 96.7 | 88.5 | 29.7 | 76.1 | 85.7 | 85.8 | 79.8 | 82.2 | 70.2 | 78.3 | |
|  | 1 |  | ← | | 91.1 | 96.8 | → | | ← | | 95.1 | 95.3 | → | |
| Stabilized | 4 |  | 95.3 | 96.7 | 97.3 | 97.4 | 87.5 | 85.5 | 92.8 | 94.6 | 94.5 | 95.2 | 93.7 | 94.8 |
| 10 mg/ml | 11 |  | 95.7 | 96.4 | 95 | 95.4 | 79.5 | 72.0 | 93.3 | 93.9 | 94 | 92.6 | 88.7 | 92 |
| of hsa | 26 |  | 96.5 | 95.5 | 96.2 | 97 | 50.5 | 35.0 | 91.8 | 92.1 | 91.2 | 90.3 | 85.4 | 74.3 |
|  | 53 |  | 95.5 | 96.6 | 94.4 | 95.9 | 33.8 | 54.9 | 87 | 86.4 | 85.4 | 85.8 | 71.2 | 78.1 |
|  | 63 |  | 95.2 | 96.0 | 94.4 | 93.4 | 32.8 | 41.2 | 84.5 | 84.1 | 81.3 | 81.3 | 76.7 | 79.0 |
|  | 1 |  | ← | | 95.3 | 96.3 | → | | ← | | 92.1 | 94.5 | → | |
| Stabilized | 4 |  | 95.7 | 96.6 | 96.3 | 97.1 | 59.4 | 17.7 | 94.8 | 94.8 | 94.7 | 94.8 | 92.2 | 74.8 |
| 5 mg/ml | 11 |  | 65.0 | 96.2 | 93.5 | 94.4 | 14.8 | NIL | 92.3 | 91.5 | 94.0 | 92.8 | NIL | NIL |
| of hsa | 26 |  | 97 | 95.7 | 88.4 | 94 | 16 | NIL | 92.2 | 92.4 | 89.6 | 88.9 | 26.9 | NIL |
|  | 53 |  | 93.6 | 95.2 | 64.9 | 70.3 | 17.2 | 12.2 | 86.7 | 89 | 80 | 79.6 | NIL | NIL |
|  | 63 |  | 93.3 | 95.5 | 70.8 | 37.8 | 6.6 | NIL | 84.7 | 84.9 | 80.5 | 65.7 | NIL | NIL |
|  | 1 |  | ← | | 81.3 | 78.5 | → | | ← | | 95.6 | 96 | → | |
| Control | 4 |  | 93.9 | 71.7 | 68.2 | 70.6 | NIL | 11 | 95.8 | 94.7 | 94.9 | 94.3 | 47.2 | 50 |
| Unstabilized | 11 |  | 86.1 | 77.3 | 35.5 | 37.9 | NIL | NIL | 94.2 | 94.9 | 86.2 | 92.0 | NIL | NIL |
|  | 26 |  | 67.8 | 71.8 | 20 | 28 | NIL | NIL | 92 | 91 | 57.9 | 76.0 | NIL | NIL |
|  | 53 |  | 73.3 | 77.2 | 10 | 9.1 | NIL | NIL | 84.2 | 87.7 | 17.7 | NIL | NIL | NIL |
|  | 63 |  | 72.8 | 79.7 | 8 | 9 | NIL | NIL | 86.8 | 85.7 | NIL | NIL | NIL | NIL |

What we claim is:

1. A solid product comprising one part by weight of fibrinogen labelled with a radioactive iodine isotope, and from 1 to 1,000 parts by weight of albumin to reduce or prevent unwanted decomposition of the fibrinogen.

2. A solid product as claimed in claim 1, wherein the fibrinogen is labelled with iodine-125.

3. A solid product as claimed in claim 1, wherein the fibrinogen is human fibrinogen and the albumin is human serum albumin.

albumin per part by weight of fibrinogen, wherein the proportion $$\frac{\text{Soluble clottable iodinated fibrinogen present}}{\text{Soluble clottable iodinated fibrinogen originally provided}}$$

remains above 0.5 during storage for one month at 2°C.

10. A solid product as claimed in claim 9, containing 20 – 1,000 parts by weight of the albumin per part by weight of the fibrinogen.

* * * * *